United States Patent [19]

Mulholland

[11] Patent Number: 5,382,243
[45] Date of Patent: Jan. 17, 1995

[54] APPARATUS WITH INDICATOR FOR ADMINISTRATION OF EYE MEDICATION

[76] Inventor: Adrian Mulholland, 1050 College Street, Duncan, British Columbia, Canada, V9L 2E7

[21] Appl. No.: 120,417

[22] Filed: Sep. 14, 1993

[51] Int. Cl.$^6$ .............................................. A61H 33/04
[52] U.S. Cl. .................................... 604/301; 604/302; 222/36
[58] Field of Search ............... 604/294, 295, 296, 297, 604/298, 299, 300, 301, 302; 222/183, 214, 336, 420; 221/155, 264, 265

[56] References Cited

U.S. PATENT DOCUMENTS

| | | | |
|---|---|---|---|
| 2,278,326 | 3/1942 | Leonard | 604/295 |
| 2,898,911 | 8/1959 | Taylor . | |
| 4,705,182 | 11/1987 | Newel-Lewis | 222/23 X |
| 5,007,905 | 4/1991 | Bauer | 604/295 |
| 5,030,214 | 7/1991 | Spector | 604/294 X |
| 5,133,702 | 7/1992 | Py | 604/302 |
| 5,154,702 | 10/1992 | Foyil | 604/298 X |
| 5,154,711 | 10/1992 | Williams | 604/301 |

OTHER PUBLICATIONS

"Method for Self-Administration of Eyedrops", Charles E. Letocha, M.D., Ann Ophthalmol 1985; 17:768–769.

"Self-Administration of Eyedrops", Gerald M. Cheldon, M.D., Ophthalmic Surgery, May, 1987, vol. 18, No. 5.

First Aid Eye Care Center brochure.

*Primary Examiner*—David Isabella
*Assistant Examiner*—Mary Beth Jones
*Attorney, Agent, or Firm*—Oyen Wiggs Green & Mutala

[57] ABSTRACT

This invention pertains to a novel apparatus which assists in administering eye medication to a patient. More particularly, this invention pertains to an apparatus which attaches to a vial containing eye medication, and detaches to assist in administering the eye medication to a patient, and accounts for a number of administrations in a day. The apparatus includes (a) a hollow truncated conical transparent shell; (b) a transparent circular plate attached to the truncated end of the conical shell wherein the plate has a circular opening in the central area of the plate; and (c) a hollow truncated conical transparent shell fitted over a portion of the exterior of the transparent shell (a).

17 Claims, 4 Drawing Sheets

FIG.1
*SECTIONAL VIEW*

APPARATUS WITH INDICATOR FOR ADMINISTRATION OF EYE MEDICATION

FIELD OF THE INVENTION

This invention pertains to a novel apparatus which assists in administering eye medication to a patient. More particularly, this invention pertains to an apparatus which detachably attaches to a vial containing eye medication, and assists in administering the eye medication to a patient, while also accounting for the number of medication administrations in a day.

BACKGROUND OF THE INVENTION

Most instruments for the alignment and dispensing of eye medications to patients are complicated and expensive. U.S. Pat. No. 5,030,214, Spector, discloses an applicator which is complicated, used while erect, and has a fluid exit. U.S. Pat. No. 5,133,702, Py, discloses a complicated instrument which uses several casings.

The basic concept of using a concave or cup-like eye medication dispenser is disclosed in U.S. Pat. No. 2,058,515. Since then, there have been several improvements, such as U.S. Pat. No. 2,898,911 which snap fits onto the body of the dispenser. U.S. Pat. No. 4,111,200 discloses an eye drop dispenser that is externally attached to the dispenser.

U.S. Pat. No. 4,733,802, Sheldon, discloses a simple cone-shaped structure, where the upper end is opaque. The structure employs an outwardly extending flange at the base, with a single opening at the base which is parallel to the upper end of the device. U.S. Pat. No. 4,946,452, Py, describes an ocular treatment apparatus.

U.S. Pat. No. 3,756,478 Pedell uses an angled tube to control the volume of medication instilled in a combination delivery and metering apparatus. Similarly, U.S. Pat. No. 3,934,585 Maurice discloses a device which meters a predetermined volume. U.S. Pat. No. 5,040,706, Davis, describes an elongated hollow body with reservoir to control dosage.

U.S. Pat. No. 5,012,496, Dreher et al. utilizes an electronic apparatus to monitor dosage, while U.S. Pat. No. 5,012,496, Weinreb et al., discloses an electronic drop counting sensor. U.S. Pat. No. 5,053,000, Booth et al., discloses a complicated device which uses electrodynamic spraying. Pumps are also used. In U.S. Pat. No. 5,152,435, Cohen, describes a dispensing pump for an applicator while U.S. Pat. No. 5,163,929, Py, utilizes a piston driven volume delivery system. U.S. Pat. No. 5,154,702, Foyil, discloses a plunger to control the delivery system from an eye dropper.

None of these devices or instruments combine the support function with an indicator or recording function. None of the patents disclose a rotating indicator sleeve which is combined with an eye medication applicator which simply and economically performs both the stated functions.

SUMMARY OF THE INVENTION

An eye medication applicator which is comprised of an instrument detachably attached to a squeeze-type medication solution bottle or other container. The instrument properly aligns the container and the eye of a patient for easy delivery of eye medication whenever required. The bottle has a body defining a volume for eye drop solution, the body having a base, a shoulder and a neck region. A nozzle defines an orifice for delivery of medication solution from the volume. The device supports the nozzle relative to an eye of the patient requiring treatment, and includes a concave device that is supported at or about the neck or any area distal of the shoulder of the dispenser bottle. The cup is contoured to conform gently to the facial tissue around the bony part of the periorbital area of the clients body, and has attached to the device a manually manipulated indicator for recording the number of times the medication solution has been administered in a specified period.

An apparatus for assisting administration of eye medication to the eye of a patient comprising: (a) a hollow truncated conical transparent shell; (b) a transparent circular plate attached to the truncated end of the conical shell, said plate having a circular opening in the central area of the plate; and (c) a hollow truncated conical transparent shell fitted over a portion of the exterior of the transparent shell (a).

An apparatus as disclosed wherein the central opening in the plate (b) has formed therein engagement means which are adapted to engage with the neck of a medication dispenser bottle which contains eye medication. The rim of the broader end of the conical shell may have an undulating configuration which is adapted to conform with the bony part of the periorbital eye area of a patient.

An apparatus as disclosed wherein the transparent outer conical shell has indicia thereon adapted to count the number of times eye medication has been administered to a patient. In the apparatus, the outer shell may be adapted to rotate manually relative to the inner shell. Stops can be formed in the inner surface of the exterior shell to enable respective positions to be maintained between the outer shell and the inner shell.

An apparatus as disclosed wherein the outer shell may be adapted to be rotated manually on the inner shell, and stops are formed in the outer surface of the inner shell to enable respective positions to be maintained between the outer shell and the inner shell.

An apparatus for use in administering eye medication to the eye of a patient comprising: (a) a hollow truncated shell having a first end a second end; (b) plate means attached to the first end of the shell and having an aperture formed in the interior region thereof; (c) a plurality of locations indicated on the exterior surface of the shell; (d) indicator means mounted on the exterior of the shell, said indicator means being moveable in relation to the shell, in relation to the indicator locations displayed on the exterior of the shell.

The shell may have a hollow conical transparent configuration. The indicator may have a hollow conical sleeve, which conforms with the exterior of the body of the conical shell, and is rotatably moveable around the exterior of the shell.

An apparatus as disclosed wherein the indicator sleeve has formed therein a window, which is adapted to display the indicator location displayed on the exterior of the conical inner shell. The second end of the sleeve may have a concave conical configuration adapted to conform with the bony portion of the orbital eye area of a patient. The indicator sleeve may have grip means formed on the exterior surface thereof. The exterior of the plate can be enlarged and have a gripping means formed therein. In the apparatus, the aperture can be circular.

An apparatus for use in administering eye medication to the eye of a patient comprising: (a) a hollow truncated shell having a first end a second end; (b) plate means attached to the first end of the shell and having an aperture formed in the interior thereof; (c) a plurality of locations indicated on the exterior surface of the shell; (d) indicator means mounted on the exterior of the shell, said indicator means being moveable in relation to the shell, in relation to the indicator locations displayed on the exterior of the shell; and (e) a dispenser bottle having a neck which is inserted through the aperture so that a dispensing tip formed in the end of the neck of the dispenser penetrates into the interior of the sleeve.

In the apparatus, a sleeve can be fitted about the neck of the dispenser bottle in order to hold the dispenser bottle in a fixed position relative to the plate and aperture of the instrument body.

BRIEF DESCRIPTION OF THE DRAWINGS

The following drawings are intended to assist in illustrating the invention and are not to be construed as restricting or limiting the spirit or scope of the invention in any way.

DETAILED DESCRIPTION OF SPECIFIC EMBODIMENTS OF THE INVENTION

The applicator supports the nozzle of a squeezable medication dispenser relative to an eye of the patient requiring treatment, and includes a hollow truncated cup-like device that may support at the neck or distally, including the annular ring, a medication container, the opposite end being contoured to conform gently to the facial tissue around on the bony eye orbit area of the periorbital area of the patient's face. The invention also includes a manual indicator or counter, wherein a ring-like indicator is attached to the exterior of the body of the applicator, and is moved manually one position on the applicator after each administration of eye medication.

Figure 1:
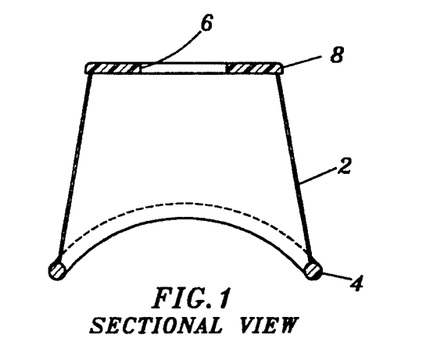
FIG. 1 illustrates a side view the applicator body.

Referring to the drawings, FIG. 1 illustrates a side view of the applicator body. The body 2 is constructed in the shape of a hollow truncated cone which has a plate 8 at the top side thereof, and a lower curved rim 4 at the bottom side thereof. The plate 8 has an aperture 6 formed in the central area thereof. The lower rim 4 of the instrument body 2 has a generally concave oval configuration, adapted to fit snuggly on the bony orbit of the eye socket region of a patient. The lower rim 4 should preferably be large enough so that the ocular pressure around the eye of the patient is minimized.

In FIG. 1 the instrument body 2 comprises a single piece of plastic material that may or may not be transparent. However, a clear or transparent body permits the administrator to see the ocular area of the patient and assists in proper positioning of the administrator on the bony eye orbit area of the patient. The rim 4 is shaped in an elliptical and concave manner adapted to fit around the periorbital area of the eye (not shown in FIG. 1 but see FIGS. 13 and 14). The rim 4 may have a beaded lip for extra comfort, and reduced localized pressure.

Figure 2:
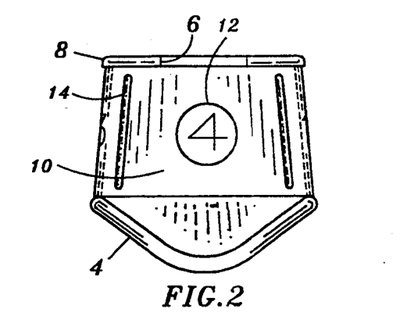
FIG. 2 illustrates a side view of the body of the applicator body with an indicator sleeve rotatably mounted on the exterior thereof.

FIG. 2 illustrates an end view of the applicator body 2 with an indicator sleeve 10 rotatably mounted thereon. As seen in FIG. 2, the indicator sleeve 10 has formed therein a circular indicator window 12, which can display numerals printed or formed on the exterior of the applicator body 2. The indicator sleeve 10 has indicator fins 14 formed on each side thereof. The indicator sleeve 10 is formed to have a hollow truncated conical shape, of the same conical angle as the conical exterior sides of the applicator body 2. In this way, the indicator sleeve 10 snuggly fits with the exterior top regions of the conical body 2. The indicator sleeve 10 can be rotatably rotated around the circumference of the exterior of the upper region of the body 2, in order to display appropriate application count numerals printed or embossed on the exterior of the body 2. As seen in FIG. 2, the indicator window 12 displays the number 4, which means that four applications of eye medication have been made to the patient during that day. The indicator number can indicate some other significant number, such as days of administration, if required.

In FIG. 2, the numbers 1 and 3 can be seen at the edges of the instrument body 2 at each side adjacent the respective indicator fins 14. The number 2 appears on the opposite side of the body 2 and is not visible in FIG. 2. As required, the indicator window 12 can be rotated so that it is positioned over either the number 1 or the number 3, in order to indicate the appropriate numerical reading.

Figure 3:
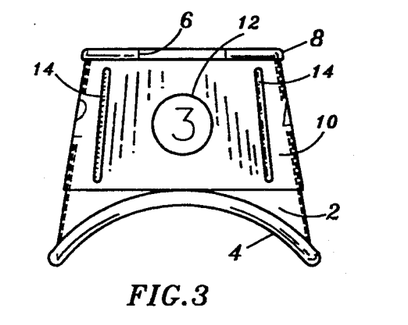
FIG. 3 illustrates a side view of the applicator body with an indicator sleeve rotatably mounted thereon.

FIG. 3 illustrates a side view of the applicator body 2 with the indicator sleeve 10 rotatably mounted thereon to a position different from that shown in FIG. 2. As seen in FIG. 3, sleeve 10 has been rotated so that the numeral 3 is displayed through the indicator window 12. The number 3 can signify the number of eyedrop administrations given that day, or some other measurement. The shoulder 8, as seen in FIG. 3, can be thicker and stronger in cross section, and if required, may be textured in order to improve gripability.

Figure 4:
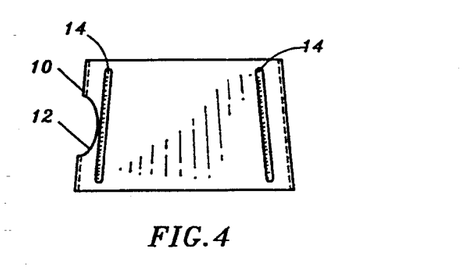
FIG. 4 illustrates a side view of the indicator sleeve, removed from the applicator.

FIG. 4 illustrates a side view of the indicator sleeve 10, with the circular indicator window 12 formed in the side thereof. The opening 12 may be a transparent lens which magnifies the numerical reading, thereby facilitating viewing by the administrator. The two fins 14 are shown at each side of the indicator sleeve 10 and facilitate gripability of the indicator sleeve 10 on the body 2 (not shown) so that it can be moved from one position to the next. If required, stops, depressions, or other engaging mechanisms, can be formed either in the instrument body 2 or the indicator sleeve 10 in order to ensure that the indicator sleeve 10 remains in a prescribed position on the exterior upper area of the instrument body 2. This ensures that the sleeve 10 will not slip out of position, thereby giving a false reading.

Figure 5:
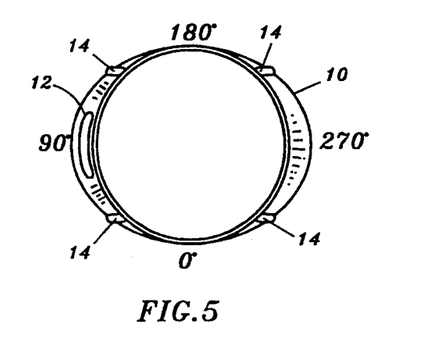
FIG. 5 illustrates a top view of the indicator sleeve.

FIG. 5 illustrates a top view of the indicator sleeve 10. As seen in FIG. 5, there are indicator fins 14 located at 45 degree, 135 degree, 225 degree, and 315 degree positions. The indicator window 12 is located at the 90 degree position. While four indicator fins 14 are shown in FIG. 5, more indicator fins may be formed in order to facilitate better gripability of the indicator sleeve 10 on the body 2 (which is not shown in FIG. 5).

Figure 6:
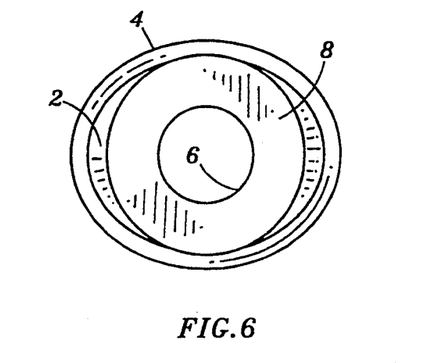
FIG. 6 illustrates a bottom view of the applicator body without the indicator sleeve rotatably mounted thereon.

FIG. 6 illustrates a bottom view of the instrument body 2, with the oval rim 4 at the bottom, a circular plate 8 formed in the top region, with a circular aperture 6 formed in the central area of the flange 8. The lower rim 4 has a generally oval concave shape. The central aperture 6 may be of any required shape in order to facilitate engagement with a medication dispenser (see alternative configurations illustrated in FIG. 8).

Figure 7A:
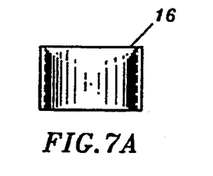
FIGS. 7a and 7b show side and top views of a spacing tube.
Figure 7B:
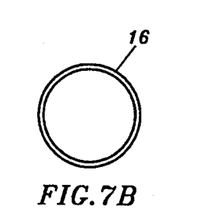

FIGS. 7a and FIG. 7b respectively illustrate side and top views respectively of a spacing tube 16, which can be used to fit over the neck of an inverted medication dispenser bottle 26, as shown subsequently in FIG. 14.

Figure 8A:
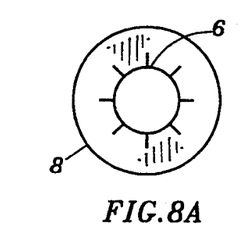
FIGS. 8a, 8b, 8c and 8d illustrate top views of alternative embodiments of applicator bodies with alternative shapes of apertures formed therein.

FIGS. 8a, 8b, 8c and 8d, illustrate top views of alternative embodiments of plates 8 with possible shapes of apertures 6 formed in the flange 8 at the top of the instrument body 2. FIG. 8a illustrates a circular aperture 6, with radial slits extending therefrom, the radial tabs formed thereby being flexibly moveable in order to enable the neck of a medication dispenser to be inserted through the aperture 6.

Figure 8B:
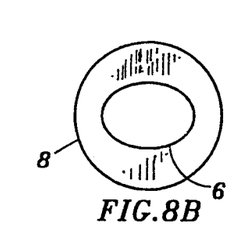

FIG. 8b illustrates an oval shaped aperture 6. The narrow sides would be flexibly moveable in order to enable the neck of a medication dispenser to be inserted there through.

Figure 8C:
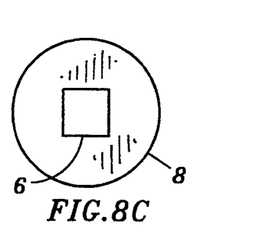

FIG. 8c illustrates a star shaped aperture 6, the plated protection projections being flexibly moveable upon engagement by the neck of a medication dispenser.

Figure 8D:
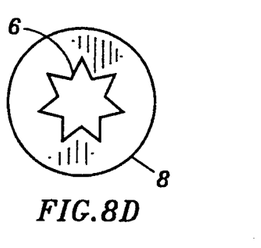

FIG. 8d illustrates a square aperture 6. This shape may be useful in accommodating a square shaped neck of a medical dispenser. It will be recognized that alternative shapes of aperture 8 can be designed in order to mate with or fit with appropriate medication dispenser necks.

Figure 9:
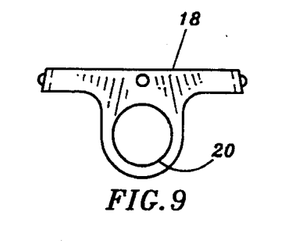
FIG. 9 illustrates a side view of an alternative embodiment of indicator sleeve.

FIG. 9 illustrates a side view of an alternative embodiment of a cut-away type indicator sleeve 18, with a framed circular window 20 formed in a projection that extends downwardly from the lower edge thereof. This design of indicator sleeve 18, with window 20, can be substituted for the indicator sleeve 10 previously described, as desired. The circular window 20 can be a magnifying lens which enlarges the number appearing underneath it on the instrument body 2.

Figure 10:
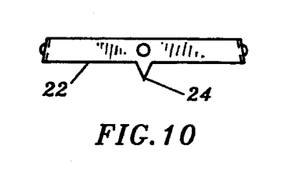
FIG. 10 illustrates a side view of a second alternative embodiment of indicator sleeve.

FIG. 10 illustrates a simplified abbreviated second alternative embodiment of indicator sleeve 22. In this design, which is very Simple, a downwardly projecting point 24 is used in place of the typical window 12 (FIG. 2 or 3) or window 20 (FIG. 9), illustrated in the previous indicator sleeve designs.

Figure 11:
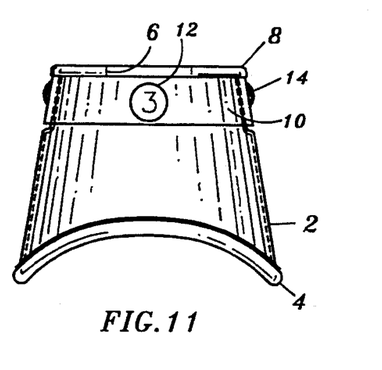
FIG. 11 illustrates a side view of an alternative rectangular shaped applicator body with an indicator sleeve mounted thereon.
Figure 12:
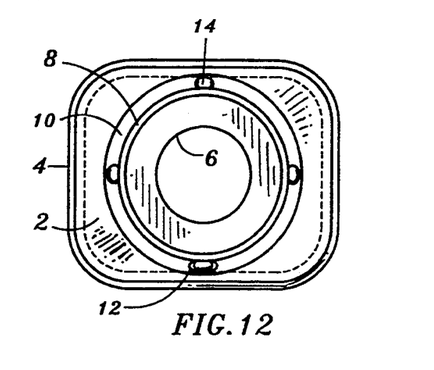
FIG. 12 illustrates a top view of an alternative rectangular shaped applicator body with an indicator sleeve thereon.

FIGS. 11 and 12 illustrate respectively side and top views of an alternative rectangular shaped applicator body 2. The rectangular shape may in certain cases be desirable to the generally conical shape previously described. Otherwise, the components of the applicator are virtually the same, except for shape. The applicator body 2, which is of a hollow rectangular shape, has a lower curved rim 4, a rectangular plate 8, with an aperture 6 formed in the central area thereof. The flange 8, as seen in FIG. 12, is circular in design. The indicator sleeve 10, while it is of a hollow rectangular construction, is constructed of a flexible material, so that it can be moved from position to position around the exterior circumference of the rectangular shaped body 2. The rectangular design may be of value in certain situations in ensuring that the indicator sleeve 10 holds its position on the exterior of the body 2. Each time the indicator sleeve 10 is moved, the corners of the rectangular body 2 move the indicator 10 into a rectangular position and hold it in that position.

Figure 13:
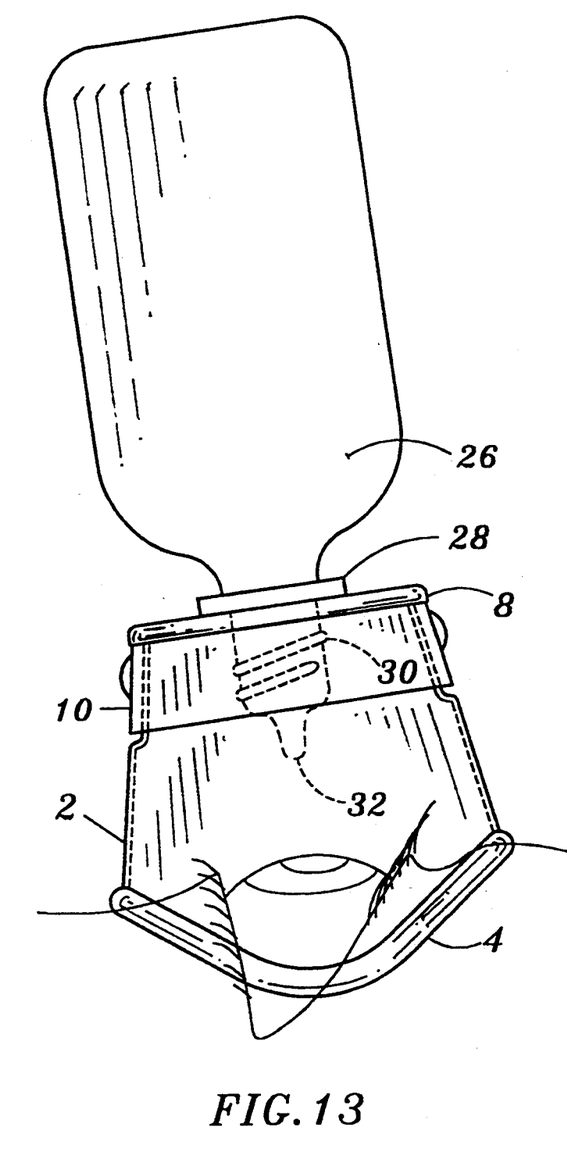
FIG. 13 illustrates a side isometric view of a medication dispenser installed in the applicator so that the dispenser can be manually squeezed to administer a drop of medication into an eye of a patient.

FIG. 13 illustrates a side isometric view of the applicator body 2 with rim 4, positioned over the bony eye orbit area of a patient. The indicator sleeve 10 is shown mounted on the upper region of the exterior of the conical body 2, below the flange 8. A medication dispenser 26 of conventional design typically as an annular ring 28 around the neck thereof. The neck of conventional dispenser 26 also typically has a spiral thread 30 around the neck thereof. As seen in FIG. 13, the dispenser 26 is inverted and the spiral thread 30 is inserted through the interior of the opening 6 in the top plate 8 of the body 2, until annular ring 28 abuts the exterior of flange 8. Then, the medication dispenser 26 is squeezed by the fingers of the administrator (not shown), to thereby squeeze a drop of medication from the interior of the dispenser 26 onto the eye of the patient. As many drops as may be required, can be administered to the eye of the patient. Once the required number of drops have been administered, then the indicator 10 is moved to the appropriate position in order to display the appropriate count numeral through the window 12.

Figure 14:
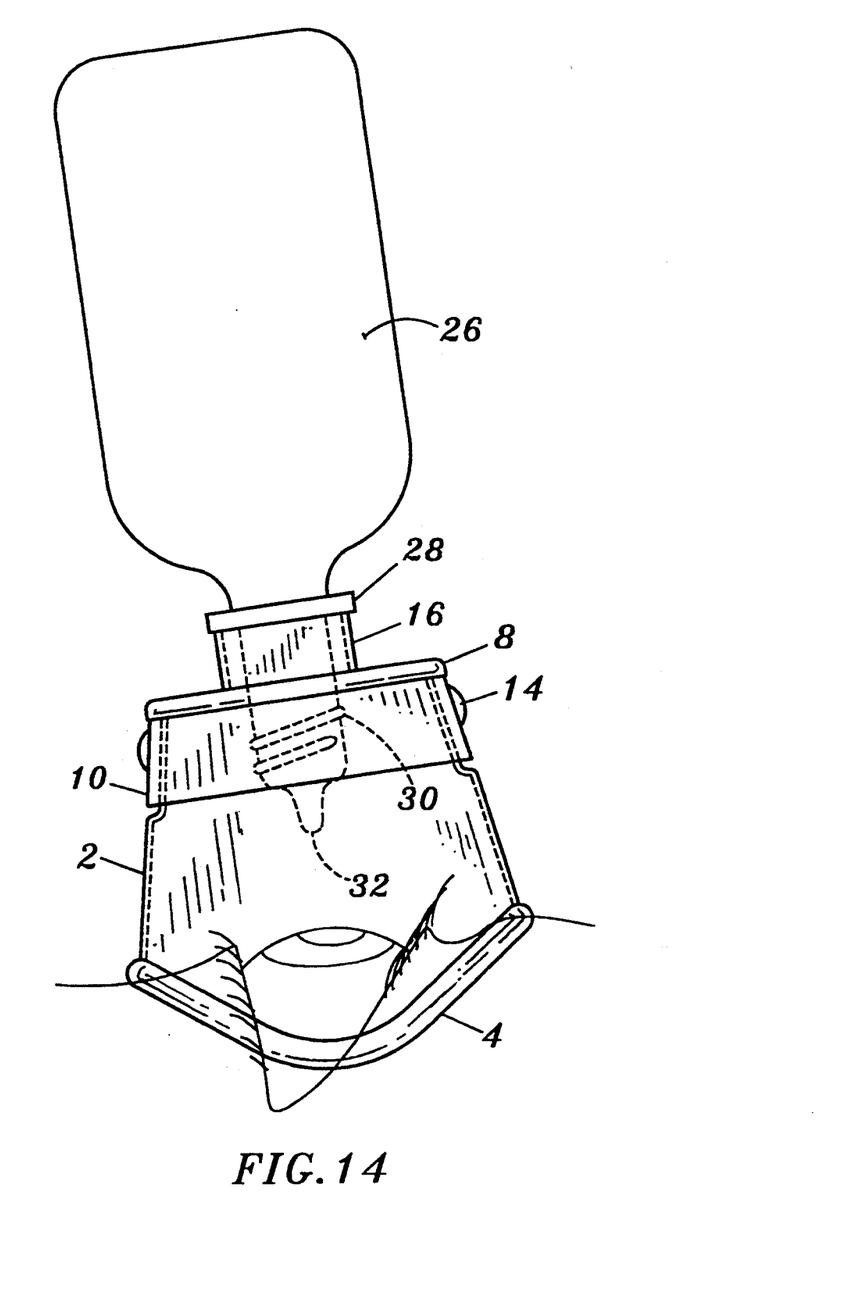
FIG. 14 illustrates a side isometric view of a medication dispenser mounted by the spacing tube in the top aperture of an applicator body, so that the dispenser can be manually squeezed to administer a drop of medication into the eye of a patient.

FIG. 14 illustrates a side isometric view of the inverted medication dispenser 26, and spiral thread 30, threaded through the interior of the opening 6 in the plate 8 of the instrument body 2. As seen in FIG. 14, a spacing tube 16 is fitted over the neck of the dispenser 26, before it is inverted, in order to hold the dispenser 26, and in particular the annular ring 28 and dispenser tip, farther away from the plate 8, and the eye of the patient. In certain cases, it may be desirable to have the tip 32 of the dispenser 26 held farther away from the lower rim 4 of the instrument body 2, and this can readily be done by utilizing a spacing tube 16. Different lengths of spacing tube 16 can be used, as required.

For packaging and shipment of a dispenser bottle 26 and applicator, the plate 8, and opening 6 therein, and the applicator body 2, together with the indicator sleeve 10 can be inverted from the position shown in FIG. 14, so that the interior of the conical body of the body 2 fits over the neck and body of the medication dispenser 26, to provide a compact combination. In this way, the instrument body 2, and indicator sleeve 10, can be distributed and marketed as a unit with a medication dispenser bottle 26. Alternatively, the two items can be packaged and purchases separately, as required.

The overall invention consists of a dispenser and positioning device combination, in which the bottles are modified, for use with positioning devices of special construction corresponding to that of the modified bottles or by integral incorporation of all or a portion only of the positioning means of the invention into the dispenser or bottle manufacture. This permits a more compact device for easy packaging, storing and safe use at all times. Typically the present bottle design may be modified at the annular ring or upper part of the dispenser to permit securing of a positioning device of the invention, consisting of a rim and body. In some instances the applicator body may be structurally reduced, perforated, or simplified by those skilled in the trade.

In another embodiment, the plate of the invention may have a neck portion with a male thread thereon which can provide closure of the applicator opening with a cap. A cap can also be placed over threads 30 to close dispenser bottle 26 and hold in it place.

In another embodiment to be completely disposable, the dispenser bottle can be modified to include the positioning means as an integral part of or partially attached near the shoulder at the upper part of an otherwise conventional container used for dispensing solution. According to another embodiment, the positioning device may be attached permanently or temporarily to the caps of the dispensing bottles, or to the dispensing nipple.

The invention may be retained for future use on the solution container by simply screwing on the cap. The device may also be retained by reversing the invention on the container. The container may also sit within the device, or be placed on top of the container for transportation.

Method of Application

In use, the cap of the dispenser bottle is carefully removed. The patient's head is slightly hyper-extended to a comfortable position while sitting in a chair, about 45 degrees, or by assuming a prone position. This position which is illustrated in FIG. 13 or 14 provides easy access to the eye for medication instillation and minimizes the drainage of medication through the tear duct. The body of the solution bottle 26 is grasped with the thumb and forefinger. The lower rim 4 of the applicator 2 is gently positioned in contact with either the lower eyelid, below the eyelid, or on or near the orbital bony ridge area by the free hand. Seating the applicator is completed by slightly rotating the lower rim 4 of the applicator to permit the other side of the lower rim 4 to gently rest on the outer surface of the open upper eyelid, or the bony orbital area, thereby stabilizing the whole unit. Preferably, if the patient is experiencing discomfort, rim 4 should be large enough that it fits over the bony eye orbital area and thereby minimizes pressure on the area adjacent the eye. A small amount of pressure may be applied to the applicator by the eye medication administrator to actually cushion the eye lid so that blinking reflexes of the patient may be deferred long enough to enable the solution to be instilled into the eye of the patient. The solution bottle with the applicator attached is elevated to as near a vertical position as possible.

The administrator or the patient may gently pull the lower eyelid down with the free hand to create a cul-de-sac, a procedure which is sometimes preferred. Therapeutic effect of the medication is usually obtained only when the drops enter the conjunctival sac, and medication is evenly distributed across the eye. Retraction of the eye lid is achieved by gentle pressure of the lid downwards against the bony orbit area which prevents pressure and trauma to the eyeball. This technique exposes the lower conjunctival sac. The patient looks up to the ceiling, which retracts the sensitive cornea up and away from the conjunctival sac, and reduces the stimulation to reflex.

It should be noted this applicator may be used with the left hand, or the right hand, and that there is no "right side" up, in the sense that one side of the lower rim 4 must face down and the other side up. The positioning of the drop into the eye is controlled by the tilt of the patient's head. The patient should position the head so it is almost horizontal, and turned slightly to the lateral side to instill the solution into the inner canthus area. This also allows the medication to run away from the nasolacrimal duct.

The applicator, by maintaining a distance between the eye drop end of the solution bottle and the eye of the patient, prevents the accidental contact of the end of the eyedropper with the eye and eye structure. This invention reduces the risk of injury to the eye and risk of transfer of infection from the eye to the dropper and its sterile contents. Contamination of the contents to another patient may injure the eye of that patient, and the container must then be discarded. After the medication is administered, the applicator is removed from the eye area, and the administrator applies gentle pressure with a finger to the nasolacrimal duct at the inner angle of the eye towards the nose for 30-60 seconds, which prevents the over flow of medication into the nasal and pharyngeal passages, absorbtion into the systemic circulation and consequent serious systemic symptoms. There should be no pressure applied directly against the eyeball at any time. The eye is then shut gently, and the patient may look down, which helps distribute the medication.

After use, the medication in the solution bottle is tightly capped by replacing the cap on the dispenser tip, thereby maintaining sterility. It should be noted that the medication solution bottle dispenser need not be dismounted from the applicator. The counter sleeve 10 is then rotated to show the number or times of the next dose required. In the morning, after the first dose is instilled, the counter is turned to the number "2", and so on. If there is only one dose a day, the indicator number may suggest the number of drops to instill per day, for example "2". Timely documentation prevents repeated or missed doses.

Features and benefits of this invention include ease and safety of instilling medication in the orbital area leaving surgically involved areas undisturbed. Height and position of the medication delivery system are designed to prevent contact between the eye and the dispenser tip of the solution bottle and also contamination from the eye. The invention avoids wastage of costly medication by enabling accurate measured instillation. The invention provides a physically stable support for those incapable of normal effective application of such eye medications, either old or young, and assists medication delivery in the absence of light or sight. Psychologically, this applicator gives the patient a sense of security and independence.

It is most desirable to discard the applicator, solution bottle and counter after the bottle contents have been completely used, or after there is no longer any need for the remaining solution. The applicator and counter are preferably constructed of inexpensive, flexible plastic which can be disposed of without substantial expense.

The present invention provides a safe, thin walled, compact, and relatively short instrument which is easily and quickly attached, either temporarily or permanently, to squeeze-type eye medication containers by utilizing most often the area between the thread of the container and the annular ring as a means of stabilizing the device, increasing the accuracy in dispensing medications or solutions.

The invention provides an inexpensive, disposable or re-useable, lightweight, economically packaged, simply produced device which overcomes the shortcomings of the prior art devices. The invention combines the above advantages with the further advantage of having a manually positionable indicator for recording the frequency or number of solution applications during a day, or specified period.

The device may be reversed and removably fixed onto the delivery system for easy transportation and storage. The bottle cap is removed and the instrument is fitted over the bottle. Replacing the cap on the delivery device fixedly attaches the instrument to the bottle preventing loss of the device or medication contents.

The invention provides an improved medication applicator that is utilized as a holder for medication containers so as to direct the medication into any portion of the eye desired by the patient. A bottle may be formed with the device integrally formed therewith as a step of manufacture. Plastic dispenser bottles, especially for ophthalmic solutions, are made in assorted sizes. Almost all consist of a spiral thread, nozzle, neck, annular ring, and shoulder.

These devices of the invention are of simple mechanical design, compact for easy storage and packaging, and are designed to be safe and easy to use. Without further analysis, many changes in details of the above described embodiments are easily introduced by applying current knowledge without altering the essential generic or specific benefits of this invention. Although only certain embodiments of the present invention have been described and illustrated, the present invention is not limited to the features of this embodiment, but includes all variations and modifications, limited only by the proper interpretation of the scope of the claims.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. An apparatus for assisting administration of eye medication to the eye of a patient comprising:
   (a) a hollow truncated conical transparent inner shell open at each end;
   (b) a transparent circular plate attached to the periphery of a truncated end of the conical shell, said plate having a circular opening in the central area of the plate; and
   (c) an exterior hollow truncated conical transparent shell rotatably fitted over a portion of the exterior of the transparent shell.

2. An apparatus as claimed 1 wherein the central opening in the circular plate has formed therein engagement means which are adapted to engage with the neck of a medication dispenser bottle which contains eye medication.

3. An apparatus as claimed in claim 2 wherein is broader than the other end and has a rim having an undulating configuration which is adapted to conform with the periorbital eye area of a patient.

4. An apparatus as claimed in claim 1 wherein the exterior of the hollow truncated conical transparent inner shell has indicia thereon adapted to indicate the number of times eye medication has been administered to a patient.

5. An apparatus as claimed in claim 4 wherein the exterior conical transparent shell is adapted to rotate manually about the exterior of the conical transparent inner shell, and stops are formed in the inner surface of the exterior shell to enable respective positions to be maintained between the outer shell and the inner shell.

6. An apparatus as claimed in claim 4 wherein the exterior shell is adapted to be rotated manually about the inner shell, and stops are formed in the outer surface of the inner shell to enable respective positions to be maintained between the outer shell and the inner shell.

7. An apparatus for use in administering eye medication to the eye of a patient comprising:
   (a) a transparent hollow truncated shell having a first open end and a second open end;
   (b) plate means attached to the first open end of the shell and having an aperture formed in a interior region thereof;
   (c) a plurality of locations indicated on the exterior surface of the hollow truncated shell; and
   (d) indicator means rotationally positioned on the exterior of the shell, said indicator means being moveable in relation to the shell to display one of the indicator locations on the exterior of the shell.

8. An apparatus as claimed in claim 7 wherein the truncated shell has a hollow conical configuration.

9. An apparatus as claimed in claim 8 wherein the indicator means is a hollow conical sleeve, which conforms with the exterior of the body of the truncated conical shell, and is rotatably moveable around the exterior of the shell.

10. An apparatus as claimed in claim 9 wherein the indicator sleeve has formed therein a window, which is adapted to display the indicator location displayed on the exterior of the conical shell.

11. An apparatus as claimed in claim 10 wherein a second end of the sleeve has a concave conical configuration adapted to conform with orbital eye area of a patient.

12. An apparatus as claimed in claim 11 wherein the indicator sleeve has grip means formed on the exterior surface thereof.

13. An apparatus as claimed in claim 12 wherein an exterior periphery of the plate is enlarged to form a rim.

14. An apparatus as claimed in claim 13 wherein the aperture is circular.

15. An apparatus as claimed in claim 14 wherein moveable tabs extending radially inward are disposed around the interior circumferences of the aperture.

16. An apparatus for use in administering eye medication to the eye of a patient comprising:
   (a) a hollow truncated shell having a first end and a second end;
   (b) plate means attached to the first end of the shell and having an aperture formed in the interior region thereof;

(c) a plurality of locations indicated on the exterior surface of the shell;
(d) indicator means mounted on the exterior of the shell, said indicator means being moveable in relation to the shell, in relation to the indicator locations displayed on the exterior of the shell; and
(e) a dispenser bottle having a neck which is inserted through the aperture so that a dispensing tip formed in the end of the neck of the dispenser penetrates into the interior of the shell.

17. An apparatus as claimed in claim 16 wherein a sleeve is fitted about the neck of the dispenser bottle in order to hold the dispenser bottle in a fixed position relative to the plate means and aperture of the instrument body.

* * * * *